United States Patent [19]
Li et al.

[11] Patent Number: 5,750,370
[45] Date of Patent: May 12, 1998

[54] NUCLEIC ACID ENCODING HUMAN ENDOTHLEIN-BOMBESIN RECEPTOR AND METHOD OF PRODUCING THE RECEPTOR

[75] Inventors: Yi Li, Gaithersburg; Craig A. Rosen, Laytonsville, both of Md.; Chandrika Kumar, West Windsor, N.J.

[73] Assignee: Human Genome Sciences, Inc., Rockville, Md.

[21] Appl. No.: 465,687

[22] Filed: Jun. 6, 1995

Related U.S. Application Data

[63] Continuation-in-part of PCT/US94/11843, Nov. 18, 1994.

[51] Int. Cl.$^6$ .................... C12N 15/12; C07H 21/00
[52] U.S. Cl. ................ 435/69.1; 536/23.5; 536/23.1; 530/350; 435/69.1; 435/335; 435/252.3; 435/320.1; 435/6; 535/52; 436/501
[58] Field of Search .................. 536/23.5, 93.1; 435/320.1, 335, 252.3, 69.1, 6; 935/52, 70, 72; 530/350; 436/501

[56] References Cited

FOREIGN PATENT DOCUMENTS 0 522 868 A1   1/1993   European Pat. Off. .

OTHER PUBLICATIONS

Hori et al, Endocrinology, 130:1885–1895, 1992.
Hosoda et al, Cell 79:1267–1276, 1994.
Corjay et al, J. Biol. Chem. 266:18771–79, 1991.
Adachi, et al., Biochemical and Biophysical Research Communications, 180(3):1267–1270 (1991).
Hayzer et al., The American Journal of the Medical Sciences, 304(4):233–238 (1992).
Hosoda, et al., Federation of European Biochemical Societies, 287(12):23–26 (1991).
Zachary, et al., The Journal of Biological Chemistry, 262(9):2947–3950 (1987).
Miller, R. et al., TIPS, 14:54–60 (1993).
Arai, H., et al., Nature, 348:730–732 (1990).
Sakurai, T., et al., Nature, 348:732–735 (1990).
Elshourbagy, N., et al., Molecular Pharmacology, 41:465–473 (1991).

*Primary Examiner*—Stephen Walsh
*Assistant Examiner*—Eliane Lazar-Wesley
*Attorney, Agent, or Firm*—Elliot M. Olstein; J. G. Mullins

[57] ABSTRACT

A human endothelin-bombesin receptor polypeptide and DNA (RNA) encoding such polypeptide and a procedure for producing such polypeptide by recombinant techniques is disclosed. Also disclosed are methods for utilizing such polypeptide for identifying agonists and antagonists to such polypeptide. Agonists to the endothelin-bombesin receptor polypeptide of the present invention may be used to treat asthma, Parkinson's Disease, acute heart failure, hypotension and osteoporosis. Antagonists against such polypeptides may be used therapeutically to treat hypertesnion, ulcerigenesis, subarachnoid hemorrhage, asthma, tumors, cyclosporin toxicity, cancer and septic shock. Also disclosed are diagnostic methods for detecting mutations in the polynucleotides of the present invention and for detecting levels of the soluble polypeptides in samples derived from a host.

21 Claims, 21 Drawing Sheets

FIG. 1A

```
         10         20         30         40         50
CCCACTATGTTGGCCAGGATGGTCTTGATTTCTTGACCTCGTGTTCTGCCCGCCTCTACC
         70         80         90        100        110
TCCCAAAGTGCCGGGATTACAGGCGTGACTGCTGCCCGGCCCCAGCATCACTTTTATA
        130        140        150        160        170
GCTTTCTGTGCCCTCTCCTCTGGGCCTTGGTGTATGAAGCCACTGCCTTTCTCTGTTGG
        190        200        210        220        230
GAAGCGAGCAGAATCAGATTGCTACTCATGATGCAGTCCGGGCAGGCATACTGTCACCT
        250        260        270        280        290
TTGGCTGTGGACACAGTTGTCAGGATAGGGGAGAAGCCCTTTAGGTCCGTCTTCTTGACA
        310        320        330        340        350
CAGCCCCTCCTACCTGGTTACGCTGGTGCTTGGTGCCTTCGCTTGGTTTAGACAACCAAGACACTTGA
        370        380        390        400        410
GAATTATGCTGTCCTCAGAAATGTCTGATGAAAAGAACAGATTCACTTTTTGGACACAATG
        430        440        450        460        470
CCCATTAGCCATCTTTGGCAGTGTTTCTGATCAAAGGTTCCCCATGCCTGCTCTAGAAA
        490        500        510        520        530
GTAAACTTTTTCAGAATAAATCCTCAAATGGATTACTGAGTAGTCTTTGCACCATTCCC
        550        560        570        580        590
ATCAGCCTAATCAGACTGAATGGTCACGCTCAGTGCAAAAAGCTGTTTGCTGTGTTAGGAT
```

FIG. 1B

```
                   610               630               650
                    .                 .                 .
GTTTCAGTGTTTCTTGTCTTTCCTGGAACAGTTCAGTGTTTAAATTTAGTAATTCAATC
                              670               690               710
                               .                 .                 .
CTGACCAGTGTAAACCCACTTAATTATTGCAGCCTAAAGAATTCAGCTACTTCTACTCTT
           730               750               770
            .                 .                 .
CATAAATGTGCCCAAGTAAATATGTGTTTTAATATTCAACCCTGGAAAATTAGTAATTC
           790               810               830
            .                 .                 .
AGATGATAAAGCTCATGTTTGGTGTCTTTGTACTCAGATTGTGAACAGGCATATTTCA
           850               870               890
            .                 .                 .
CTGATTTAGACTTAGTATACTTGATGAGAATGCTCAGGTTGAAGAGATAGTTCTGTCAGC
           910               930               950
            .                 .                 .
AATCCAACATCTATAGCAATGTGGAAAAAGTAATCAACTCATATTTCACGAATTTGATGT
           970               990              1010
            .                 .                 .
ATGTTGTGATTTAGAGGGCATGAGAGATAAAGTTTATATTTGAACTGTGTGGGGTAGGGGA
          1030              1050              1070
            .                 .                 .
AGAAGAGGTTGCTTAAGCAAATGGGGGTGATTGAGGAACAAGATGTCTCTAAGATGAG
          1090              1110              1130
            .                 .                 .
AAGTTATTTCTTGCATCATAGAAGCACTCTCCACCCGGGAGTGATTGTGTTAACTAT
          1150              1170              1190
            .                 .                 .
AAATCATTTATATCTGTACATTAAAGCAGATTCCCTCAATTAGGCAAATTTGGTTAGCCA
```

FIG. 1C

```
         1210           1230          1250
AGCCCAAGTTATTGTTTGTACTGAAGTAATAAAGCTGCATTTCCTTAAAATATATTC
         1270          1290          1310
TGTAGTTAAGACTTTGTCTTGCTTTCCGGAATTCCTGTGTTTTCTTTCCTCTAGACCT
         1330          1350          1370
CGGCTTGCAACTGGATCAAACGCTGTCGAAAGGATGTAAATAGGCAGAGCAACTGTTACC
         1390          1410          1430
AAGAAGGCCACCACCCCCACCCAAAGGCAGTGAGGAGTGTGGGGCTTCGTCTGGGCTCCC
         1450          1470          1490
CCGAGTCTCAACAGTAATCAACAGTCAGGTGTTGATTGCAACTTTTCAAGGTCAGCCACC
         1510          1530          1550
GGGAGTAGCCTATTCCCTCTAGGAACCTTGCTGGAGGCATACCTTGCTGGACTCAACTTGG
         1570          1590          1610
CTGAGAAATGCACAAGATGCCAAAGGAGGAAGGATTATAGGGGCGTGTGTGTGACCCCC
         1630          1650          1670
AAGACCGATCTTCCGCTATCACCCTAATCTCCGGTTCCCCGCTACCCGGGGCGGGGGTGAG
         1690          1710          1730
TATGTGACATGTGCCTAACTCTCAGCAGCAACTTCGGCAGCAGGTGTCGATCCTAACTAA
         1750          1770          1790
GCAGGAGCTGCCGGGGTGCCCTCAACCAAGCCATGCGAGCCCCGGGGCGGCCTTC
```

FIG. 1D

```
                                      M   R   A   P   G   A   L   L
                                                      1850
TCGCCCGCATGTCGCGGGCTACTGCTTCTGCTACTGCTTCTGCAAGGTGTGTCTGCCTCTTCTGCCC
 A   R   M   S   R   L   L   L   L   L   L   K   V   S   A   S   S   A   L
                 1870                            1890                   1910
TCGGGGTCGCGCCCCTGCGTCCAGAAACGAAACTGTCTGGGGAGAGCTGTGCACCTACAG
 G   V   A   P   A   S   R   N   E   T   C   L   G   E   S   C   A   P   T   V
                 1930                            1950                   1970
TGATCCAGCGCCGCGGCCAGGACGCCCTGGGGACCGGGAAATTCTGCAAGAGACGTTCTGC
 I   Q   R   R   G   R   D   A   W   G   P   G   N   S   A   R   D   V   L   R
                 1990                            2010                   2030
GAGCCCGAGCCACCCAGGAGGAGCAGGGGCAGCCGTTCTTGCGGGAGCCCTCCTGGGACC
 A   R   A   P   R   E   E   Q   G   A   A   F   L   A   G   P   S   W   D   L
                 2050                            2070                   2090
TGCCGGCGGCCCCGGACCCGTGACCCGGCTGCAGGAGGGGCCGGAGCGGTCGACAGCCG
 P   A   A   P   D   R   D   P   A   A   G   R   G   A   E   A   S   T   A   G
                 2110                            2130                   2150
GACCCCCGGGACCTCCAACCAGGCCACCTGTCCCCTGGAGGTGGAAAGGTGCTCGGGGTC
 P   P   G   P   P   T   R   P   P   V   P   W   R   W   K   G   A   R   G   Q
                 2170                            2190                   2210
AGGAGCCTTCTGAAACTTTGGGGAGAGGGAACCCCACGGCCCTCCAGCTTCTTCCTTCAGA
 E   P   S   E   T   L   G   R   G   N   P   T   A   L   Q   L   F   L   Q   I
                 2230                            2250                   2270
```

FIG. 1E

```
TCTCAGAGGAGGAAGAGAAGGGTCCCAGAGGCCGCTGTCATTTCCGGGCTAGCCAGGAGC
 S  E  E  E  E  K  G  P  P  R  G  A  V  I  S  G  R  S  Q  E  Q
         2290                    2310                    2330
AGAGTGTGAAGACAGTCCCCGGAGCCAGCGATCTTTTTACTGTCAAGGAGAGCCGGGA
 S  V  K  T  V  P  G  A  S  D  L  F  Y  C  P  R  R  A  G  K
         2350                    2370                    2390
AACTCCAGGGTTCCCACCACAAGCCCCTGTCCAAGACGGCCAATGACTGGCGGGGCACG
 L  Q  G  S  H  H  K  P  L  S  K  T  A  N  G  L  A  G  H  E
         2410                    2430                    2450
AAGGGTGGACAATTGCACTCCCCGGGCGCTGGCCCAGAATGGATCCTTGGGTGAAG
 G  W  T  I  A  L  P  G  R  A  L  A  Q  N  G  S  L  G  E  G
         2470                    2490                    2510
GAATCCATGATCCTGGGGGTCCCCGCGGGAAACAGCACGAACCGGGTGTGAGACTGA
 I  H  D  P  G  G  P  R  R  G  N  S  T  N  R  R  V  R  L  K
         2530                    2550                    2570
AGAACCCCTTCTACCCGCTGACCCAGGAGTCCTATGGAGCCTACGCGGTTCATGTGTCTGT
 N  P  F  Y  P  L  T  Q  E  S  Y  G  A  Y  A  V  M  C  L  S
         2590                    2610                    2630
CCGTGGTGATCTTCGGGACCGGCATCATTGGCAACCTGGCGGTGATGTGCATCGTGTGCC
 V  V  I  F  G  T  G  I  I  G  N  L  A  V  M  C  I  V  C  H
         2650                    2670                    2690
ACAACTACTACATGCGGAGCATCTCCAACTCCCTCTTGGCCAACTGGTCTTCTGGGACT
```

TTCTCATCATCTTCTTCTGCCTTCCGCTGGTCATCTTCCACGAGCTGACCAAGAAGTGGC
 L  I  F  F  C  L  P  L  V  I  F  H  E  L  T  K  K  W  L
       2770              2790              2810

TGGTGGAGGACTTCTCCTGCAAGATCGTGCCCTATATAGAGGTCGCTTCTCTGGGAGTCA
 V  E  D  F  S  C  K  I  V  P  Y  I  E  V  A  S  L  G  V  T
       2830              2850              2870

CCACTTTCACCTTATGTGCTCTGTGCATAGACCGCTTCCGTGCCGCCACCAACGTACAGA
 T  F  T  L  C  A  L  C  I  D  R  F  R  A  A  T  N  V  Q  M
       2890              2910              2930

TGTACTACGAAATGATCGAAAACTGTTCCTCAACAACTGCCAAACTGCTGTTATATGGG
 Y  Y  E  M  I  E  N  C  S  S  T  T  A  K  L  A  V  I  W  V
       2950              2970              2990

TGGGAGCTCTATTGTGTTAGCACTTCCAGAAGTTGTTCTCCGCCAGCTGAGCAAGGAGGATT
 G  A  L  L  L  A  L  P  E  V  V  L  R  Q  L  S  K  E  D  L
       3010              3030              3050

TGGGGTTTAGTGGCCGAGCTCCGGCAGAAAGGTGCATTATTAAGATCTCTCCTGATTTAC
 G  F  S  G  R  A  P  A  E  R  C  I  I  K  I  S  P  D  L  P
       3070              3090              3110

CAGACACCATCTATGTTCTAGCCCTCACCTACGACAGTGCGAGACTGTGGTGGTATTTTG
 D  T  I  Y  V  L  A  L  T  Y  D  S  A  R  L  W  W  Y  F  G
       3130              3150              3170
```

FIG. 1G

```
GCTGTTACTTTTGTTGCCCACGCTTTCACCATCACCTGCTCTCTCAGTGACTGCGAGGA
 C  Y  F  C  L  P  T  L  F  T  I  T  C  S  L  V  T  A  R  K
         3190                    3210                    3230

AAATCCGCAAAGCAGAGAGAAAGCCTGTACCCGAGGGAATAAACGGCAGATTCAACTAGAGA
 I  R  K  A  E  K  A  C  T  R  G  N  K  R  Q  I  Q  L  E  S
         3250                    3270                    3290

GTCAGATGAACTGTACAGTAGTGGCACTGACCATTTTATATGGATTGGGCATTATTCCTG
 Q  M  N  C  T  V  V  A  L  T  I  L  Y  G  L  G  I  I  P  E
         3310                    3330                    3350

AAAATATCTGCAACATTGTACTGCCTACAGGGGTTTCACAGCAGACAATGG
 N  I  C  N  I  V  T  A  Y  M  A  T  G  V  S  Q  Q  T  M  D
         3370                    3390                    3410

ACCTCCTTAATATCATCAGCCAGTTCCTTTTGTTCTTTAAGTCTTGTGTCACCCCAGTCC
       L  L  N  I  I  S  Q  F  L  L  F  F  K  S  C  V  T  P  V  L
                 3430                    3450                    3470

TCCTTTTCTGTCTCTGCAAACCCTTCAGTCGGGCCTTCATGGAGTGCTGCTGCTGTTGCT
 L  F  C  L  C  K  P  F  S  R  A  F  M  E  C  C  C  C  C  C
         3490                    3510                    3530

GTGAGGAATGCATTCAGAAGTCTTCAACGGTGACCAGTGATGACAATGACAACGAGTACA
 E  E  C  I  Q  K  S  S  T  V  T  S  D  D  N  D  N  E  Y  T
         3550                    3570                    3590

CCACGGAACTCTCGAACTCTCGGCCTTTCAGTGCCATACGCCGTGAAAGTGTCCACTTTTGCTT
```

FIG. 1H

```
T  E  L  E  L  S  P  F  S  A  I  R  R  E  M  S  T  F  A  S
   3610              3630              3650
CTGTCGGAACTCATTGCTGAAGGACAGTACTGGTTGGTCAGATTTATTTGTTTGATTT
V  G  T  H  C  *
   3670              3690              3710
TCATATCCCGTGAAAGTTTTAATTCATATTTTCCTTATAGGAAAAATGCAAAAAAGA
             3730              3750              3770
AACAATAAAGAAAGAATATTAACTACTGTAGAACTGATTTTACAAATTAATATTGTGC
             3790              3810              3830
TTTGAAAAAAAGTTTCTATTTAGTTATTTAAGAAGAATGAGAAGGCCAATAGTTTAGAT
             3850              3870              3890
TATTTATCTGGTATGGTGCTAAATATTTTATTGAAAAAAGTTACTGCAACTTAACTTAA
             3910              3930              3950
AATTGCTAACGTTTTTTCTCTCTTTTAAAAATACAATTATTGTATATTAATTATAGCAATG
             3970              3990              4010
TGATTTGTAGGTTATTTTATATTGAGTTGTGATTGAAGTATGTTGTATATGGTATTG
             4030              4050              4070
TGAGATGATTTGTACTTGGAAGCATTCACAAGTAGCACCAAATAAATTACACTTTATTC
             4090              4110              4130
TTTAAATGTCATTGTCAATCTACTTTTAACCAATATTCAATAAATCTTCTAATTGCCTTAA
             4150
AAAAAAAAAAAAAA
```

```
- - - - A C - - S - - -    Majority
    40              50
C L G E S C A P T V I Q    49.pep.4/29
- - - - G C V I S D - -    HumanETA.PEP
- - - - A C G L S R I W    HuETBR.PEP
- - - - A C L M V G V C    FROG.ET3R.PEP
- - - - - - - - - - - -    GRP-R
- - - - - - - - - - - -    NeuroMBR/rat

- X X X S - D - - - - -    Majority
    90             100
P A A P D R D P A A G R    49.pep.4/29
- - - - - S - - - - - -    HumanETA.PEP
W P K G S N A - - - - -    HuETBR.PEP
V Q L D S - - - - - - -    FROG.ET3R.PEP
- H S A D - - - - - - -    GRP-R
- E V W E N D - - - - -    NeuroMBR/rat

- - - - - - F L P X S D    Majority
    140            150
P T A L Q L F L Q I S E    49.pep.4/29
- - - - - - F L V T T H    HumanETA.PEP
- - - - - - S L A R S L    HuETBR.PEP
- - - - - - - I Q N N      FROG.ET3R.PEP
- - - - - - - L P V N D    GRP-R
- - - - - - F L P D S D    NeuroMBR/rat

- - - - - - - - - - - -    Majority
    190            200
L Q G S H H K P L S K T    49.pep.4/29
- - - - - - - - - - - -    HumanETA.PEP
- - - - - - - - - - - -    HuETBR.PEP
- - - - - - - - - - - -    FROG.ET3R.PEP
- - - - - - - - - - - -    GRP-R
- - - - - - - - - - - -    NeuroMBR/rat
```

```
- - - - - - - K I K X A    Majority
        240           250
N S T N R R V R L K N P    49.pep.4/29
- - - - - - T K I T S A    HumanETA.PEP
- - - - - - I E I K E T    HuETBR.PEP
- - - - - - A K I R H A    FROG.ET3R.PEP
- - - - - - - - - P G I    GRP-R
- - - - - - - - - E L V    NeuroMBR/rat N K Y M R N G P N I L I    Majority
        290           300
N Y Y M R S I S N S L L    49.pep.4/29
N K Y M R N G P N A L I    HumanETA.PEP
N K C M R N G P N I L I    HuETBR.PEP
N K C M R N G P N V L I    FROG.ET3R.PEP
V K S M R N V P N L F I    GRP-R
N S T M R S V P N I F I    NeuroMBR/rat G C K L V P F I Q L A S    Majority
        340           350
- C K I V P Y I E V A S    49.pep.4/29
L C K L F P F L Q K S S    HumanETA.PEP
M C K L V P F I Q K A S    HuETBR.PEP
- - - I Y Q L V H L Y R    FROG.ET3R.PEP
G C K L I P F I Q L T S    GRP-R
G C K L I P A I Q L T S    NeuroMBR/rat A V L I W V V S V L L A    Majority
        390           400
L A V I W V G A L L L A    49.pep.4/29
I V S I W I L S F I L A    HumanETA.PEP
I V L I W V V S V V L A    HuETBR.PEP
L T L I W A V A I I V A    FROG.ET3R.PEP
A A F I W I I S M L L A    GRP-R
A V G I W V V S V L L A    NeuroMBR/rat
```

```
- - - - - Y Q K A K S W    Majority
          440       450
V L A L T Y D S A R L W    49.pep.4/29
- - - - - Y Q D V K D W    HumanETA.PEP
- - - - - Y K T A K D W    HuETBR.PEP
- - - - - Y Q E V K V W    FROG.ET3R.PEP
- - - - - H P K I H S M    GRP-R
- - - - - H P K I H S V    NeuroMBR/rat N D H L K Q Q - - - R R    Majority
      490         500
T R G N K R Q I Q L E S    49.pep.4/29
S E H L K Q - - - - R R    HumanETA.PEP
N D H L K Q - - - - R R    HuETBR.PEP
N D H M K Q - - - - R R    FROG.ET3R.PEP
N I H V K K Q I E S R K    GRP-R
N E H T K Q M E T R K      NeuroMBR/rat

- - - - R S C E L - E I    Majority
      540         550
- - - - - - - - - - - M    49.pep.4/29
- M D K N R C E L - - -    HumanETA.PEP
- N D P N R C E L - - -    HuETBR.PEP
L K N K R S C I M A E I    FROG.ET3R.PEP
- - - - R S Y H Y S E V    GRP-R
- - - - R S F N Y K E I    NeuroMBR/rat K N C F N S C L C C C C    Majority
      590         600
S R A F M E C C C C C C    49.pep.4/29
K N C F Q S C L C C C C    HumanETA.PEP
K N C F K S C L C C W C    HuETBR.PEP
K N C F Q S C L C C W C    FROG.ET3R.PEP
R K Q F N T Q L L C C Q    GRP-R
R K H F N S Q L C C G Q    NeuroMBR/rat
```

| | | | | | | | | | | | | | | | | | |
|---|---|---|---|---|---|---|---|---|---|---|---|---|---|---|---|---|---|
|569| E | E | C |I| Q |K|S| S | T | - | V |T|S| D | D | N | D |N|
|389| - | - |Y| Q | S |K|S| - | - | - |L| M | T |S| V | P | M |N|
|406| Q |S| F | E |E|K| Q | - | - | - | - | - | - |S| L | E |E| K |
|403| H | - | - | R | P | T | L | - | - | - | T | I | T | P | M | D |E| K |
|342| P | G | L |I| I | R |S| H | S | - | - |T| G | R |S| T | T | C |
|344| K |S|Y| P |E| R |S| T | S | Y |L| L |S|S|S| A | V | R |

Decoration 'Decoration #1': Shaded with solid residues that match the Consensus exactly.

```
    G T S L K S K A N D V X T D S - L N S G
              |                 |
             620               630
```

| | | | | | | | | | | | | | | | | | | | |
|---|---|---|---|---|---|---|---|---|---|---|---|---|---|---|---|---|---|---|---|
| E | Y | T | T | E | L | E | L | S | P | F | S | A | I | R | R | E | M |S| T |
|G|T|S| I | Q | W |K|N|H|D| Q | N | N | H | - | - | - |N| T | D |
| Q | S | C |L| K | F |K|A|N|D| H | G | Y |D| - | - | - |N| F | - |
|G|S| G | G | K | W |K|A|N| G | H | D | L |D| L | D | R |S|S| S |
| M |T|S| L | K | S | T | N | P | S |V| A |T| F | S | - |L| I | N |G|
| M |T|S| L | K | S | N |A| K | N | V | V |T| N | S | V |L| L | N |G|

```
    R S S N K E S S S                Majority
        |
       640
```

| | | | | | | | | | |
|---|---|---|---|---|---|---|---|---|---|
| F | A |S| V | G | T | H | C |   | 49.pep.4/29 |
|R|S|S| H | K | D |S| M | N | HumanETA.PEP |
|R|S|S|N|K| Y |S|S|S| HuETBR.PEP |
|R| L |S|N|K| Y |S|S|S| FROG.ET3R.PEP |
| N | I | C | - | H |E| R | Y | V | GRP-R |
| H |S| T | K | Q |E| I | A | L | NeuroMBR/rat |

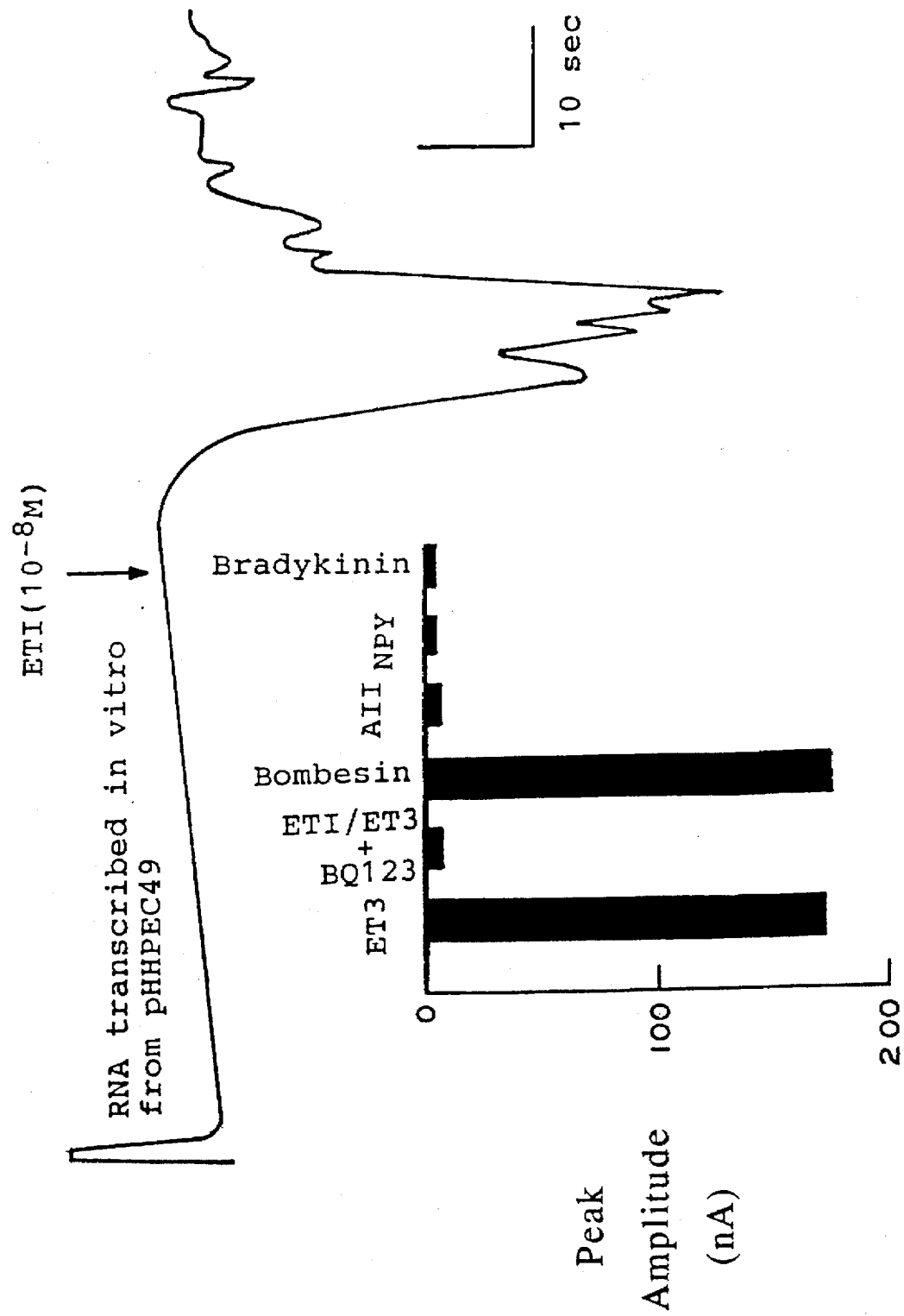

NUCLEIC ACID ENCODING HUMAN ENDOTHLEIN-BOMBESIN RECEPTOR AND METHOD OF PRODUCING THE RECEPTOR

This application is a continuation-in-part of PCT/US94/11843 filed Nov. 18, 1994.

This invention relates to newly identified polynucleotides, polypeptides encoded by such polynucleotides, the use of such polynucleotides and polypeptides, as well as the production of such polynucleotides and polypeptides. More particularly, the polypeptide of the present invention is a human 7-transmembrane receptor. The transmembrane receptor is a G-protein coupled receptor. More particularly, the 7-transmembrane receptor has been putatively identified as an endothelin-bombesin receptor, sometimes hereinafter referred to as "ETBR." The invention also relates to inhibiting the action of such polypeptides.

It is well established that many medically significant biological processes are mediated by proteins participating in signal transduction pathways that involve G-proteins and/or second messengers, e.g., cAMP (Lefkowitz, Nature, 351: 353–354 (1991). Herein these proteins are referred to as proteins participating in pathways with G-proteins or PPG proteins. Some examples of these proteins include the GPC receptors, such as those for adrenergic agents and dopamine (Kobilka, B. K., et al., PNAS, 84: 46–50 (1987); Kobilka, B. K., et al., Science, 238: 650–656 (1987); Bunzow, J. R. et al., Nature, 336: 783–787 (1988)), G-proteins themselves, effector proteins, e.g., phospholipase C, adenyl cyclase, and phosphodiesterase, and actuator proteins, e.g., protein kinase A and protein kinase C (Simon, M. I., et al., Science, 252: 802–8 (1991)).

For example, in one form of signal transduction, the effect of hormone binding is activation of an enzyme, adenylate cyclase, inside the cell. Enzyme activation by hormones is dependent on the presence of the nucleotide GTP, and GTP also influences hormone binding. A G-protein connects the hormone receptors to adenylate cyclase. G-protein was shown to exchange GTP for bound GDP when activated by hormone receptors. The GTP-carrying form then binds to an activated adenylate cyclase. Hydrolysis of GTP to GDP, catalyzed by the G-protein itself, returns the G-protein to its basal, inactive form. Thus, the G-protein serves a dual role, as an intermediate that relays the signal from receptor to effector, and as a clock that controls the duration of the signal.

The peptide endothelin is a peptide of 21 amino acid residues and performs in vivo effects via endothelin receptors. Endothelin (ET) is a peptide present in various tissues in animals and is known as a strong vasoconstrictor. ET is one peptide of a family of at least 4 mammalian peptides characterized by 2 disulphide bridges and 6 conserved amino acid residues at the C-terminus.

Members of the family are called endothelin-1 (ET-1), endothelin-2 (ET-2), and endothelin-3 (ET-3). A fourth peptide, vasointestinal contractor, is also sometimes described as the murine or rat form of ET-2. They differ mostly in the 29-membered ring system formed by the Cys-3-Cys-11 disulphide bond. Endothelins are produced by metabolism of a preproendothelin to a proendothelin, which is itself metabolized to the mature endothelin. The cleavage of proendothelin is thought to be due to the activity of a specific enzyme. ETs are distributed in a wide variety of vascular and non-vascular tissues (PNAS, USA, 86: 2863–2867 (1989)).

It has previously been shown in vivo that ET-1 and ET-2 are much stronger vasoconstrictors than ET-3, whereas the three ET isopeptides are roughly equipotent in producing the transient vasodilation. The analysis of nucleic acid sequences of ETs has revealed that various kinds of ET isopeptides exist. These ET isopeptides are also different in their properties. Therefore, it appears that various sub-types of ET-receptors exist. The existence of various sub-types of ET-receptors has been proven by the radioactive ligand binding studies of Watanabe, H., et al., Biochem-Biophys, Res. Commun., 161: 1252–1259 (1989), and Martin, E. R., et al., J. Biol. Chem., 265: 14044–14049 (1990). These studies indicate the existence of at least two kinds of ET-receptors. One of them has a higher affinity for ET-1 and ET-2 than for ET-3 and the other has an affinity for ET-1, ET-2 and ET-3 with no cell activity. The $ET_A$ receptors have a lower affinity for ET-3 and the $ET_B$ receptors are nonselective.

The receptors are homologous to other heptahelical receptors of the rhodopsin superfamily, having 7 hydrophobic regions predicted to form transmembrane helices.

The placenta has a very high expression of both receptors, as does the lung. In general the non-selective $ET_B$ receptor seems to be more widely expressed (e.g., in liver, kidney and uterus) and is probably the more prominent receptor in the CNS, a result that agrees with binding and functional studies. The heart is the only tissue about which thee is a consensus that an $ET_A$-type receptor predominates. The $ET_A$ receptors are associated with blood vessels and $ET_B$ receptors with glial, epithelial and ependymal cells, but few, if any, are associated with neurons. In the kidney, $ET_A$ receptors are located on blood vessel smooth-muscle cells, and $ET_B$ receptor expression occurs on a glomerular endothelium, vasa recti and the thin segments of Henle's loops.

Endothelins elicit biological responses by various signal transduction mechanisms, including the G-protein-coupled activation of phospholipase C and the activation of voltage-dependent $Ca^{2+}$ channels (Kasuya, Y., et al., Biochem. Biophys. Res. Commun., 61: 1049–1055 (1989)). Thus, different sub-types of the endothelin receptor may use different signal-transduction mechanisms. Endothelin receptors have a relatively long N terminus preceding transmembrane segment I, and this portion may be involved in binding a relatively large endothelin peptide.

Applicants have discovered a G-protein coupled receptor which has hydropathicity and amino acid homology which shows the existence of the 7 hydrophobic segments and a significant sequence similarity with other G-protein-coupled receptors. The 7 membrane-spanning domains and extracellular N-terminus and cytoplasmic C-terminus have also been identified.

The G-protein coupled receptor of the present invention has been putatively identified as an endothelin-bombesin receptor as a result of its homology to the known endothelin receptors $ET_A$ and $ET_B$ and as a result of its ability to bind endothelin and bombesin.

In accordance with one aspect of the present invention, there is provided a novel putative mature polypeptide which is a G-protein coupled receptor, as well as fragments, analogs and derivatives thereof. The polypeptide of the present invention is of human origin.

In accordance with another aspect of the present invention, there are provided polynucleotides (DNA or RNA) which encode such polypeptides.

In accordance with yet a further aspect of the present invention, there is provided a process for producing such polypeptides by recombinant techniques.

In accordance with yet a further aspect of the present invention, there is provided a process for utilizing such polypeptides, or polynucleotides encoding such polypeptides for therapeutic purposes, to measure the concentration of endothelin in vivo, or in soluble form as an antagonist.

In accordance with yet a further aspect of the present invention, there are provided antibodies against such polypeptides.

In accordance with yet another aspect of the present invention, there are provided antagonists to such polypeptides, which may be used to inhibit the action of such polypeptides.

In accordance with still another embodiment, there is provided a process of using the receptor to screen for receptor antagonists and/or receptor agonists and/or receptor ligands.

There and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIG. 1 shows the cDNA sequence (SEQ ID NO:1) and the corresponding deduded amino acid sequence (SEQ ID NO:2) of the G-protein coupled receptor of the present invention. The first 26 amino acids represent a putative signal sequence. The standard one-letter abbreviation for amino acids is used.

FIG. 3 illustrates an amino acid alignment of the G-protein coupled receptor of the present invention and endothelin receptors from various species of animals. Faded areas are those areas which match with the other amino acid sequences in the figure.

FIG. 4 shows that ET1, ET3 and Bombesin induced chloride currents in oocytes injected with pHHPEC49 derived RNA transcripts. The trace shows ET1 mediated chloride current (nanoamps). Arrow indicates ET1 addition. The inset shows the mean peak responses to 10 nM AII, Neuropeptide Y (NPY) and Bradykinin. The mean peak ±S.E. peak current response to ET1 is 150±50 (n=75), ET2 156±55 (n=75) and Bombesin 148±47 (n=75).

Figure 2A:
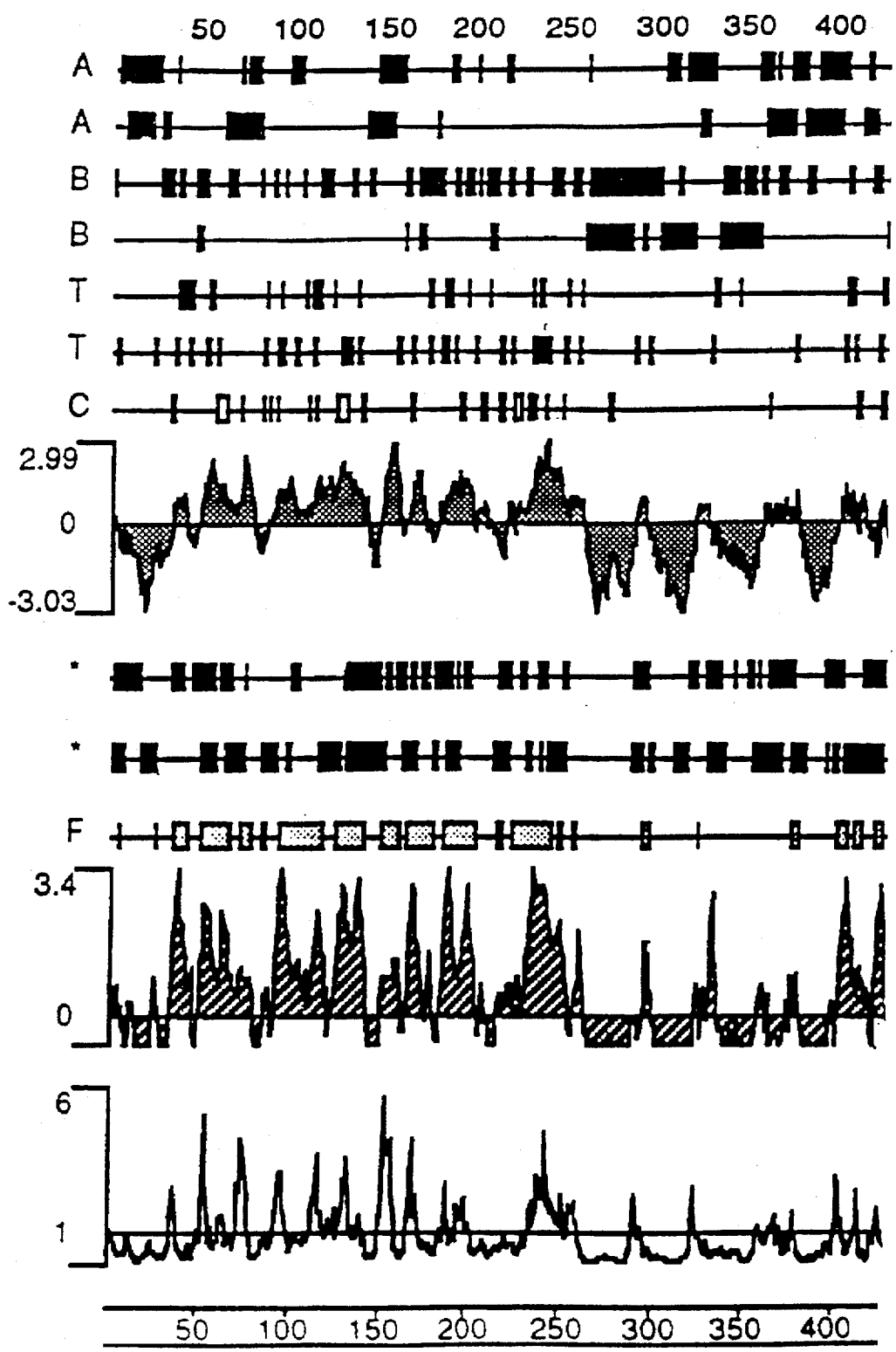
FIG. 2 is an illustration of the secondary structural features of the G-protein coupled receptor. The first 7 illustrations set forth the regions of the amino acid sequence which are alpha helices, beta sheets, turn regions or coiled regions. The boxed areas are the areas which correspond to the region indicated. The second set of figures illustrate areas of the amino acid sequence which are exposed to intracellular, cytoplasmic or are membrane-spanning. The hydrophilicity part illustrates areas of the protein sequence which are the lipid bilayer of the membrane and are, therefore, hydrophobic, and areas outside the lipid bilayer membrane which are hydrophilic. The antigenic index corresponds to the hydrophilicity plot, since antigenic areas are areas outside the lipid bilayer membrane and are capable of binding antigens. The surface probability plot further corresponds to the antigenic index and the hydrophilicity plot. The amphipathic plots show those regions of the 13 sequences which are polar and non-polar. The flexible regions correspond to the second set of illustrations in the sense that flexible regions are those which are outside the membrane and inflexible regions are transmembrane regions.
Figure 2B:
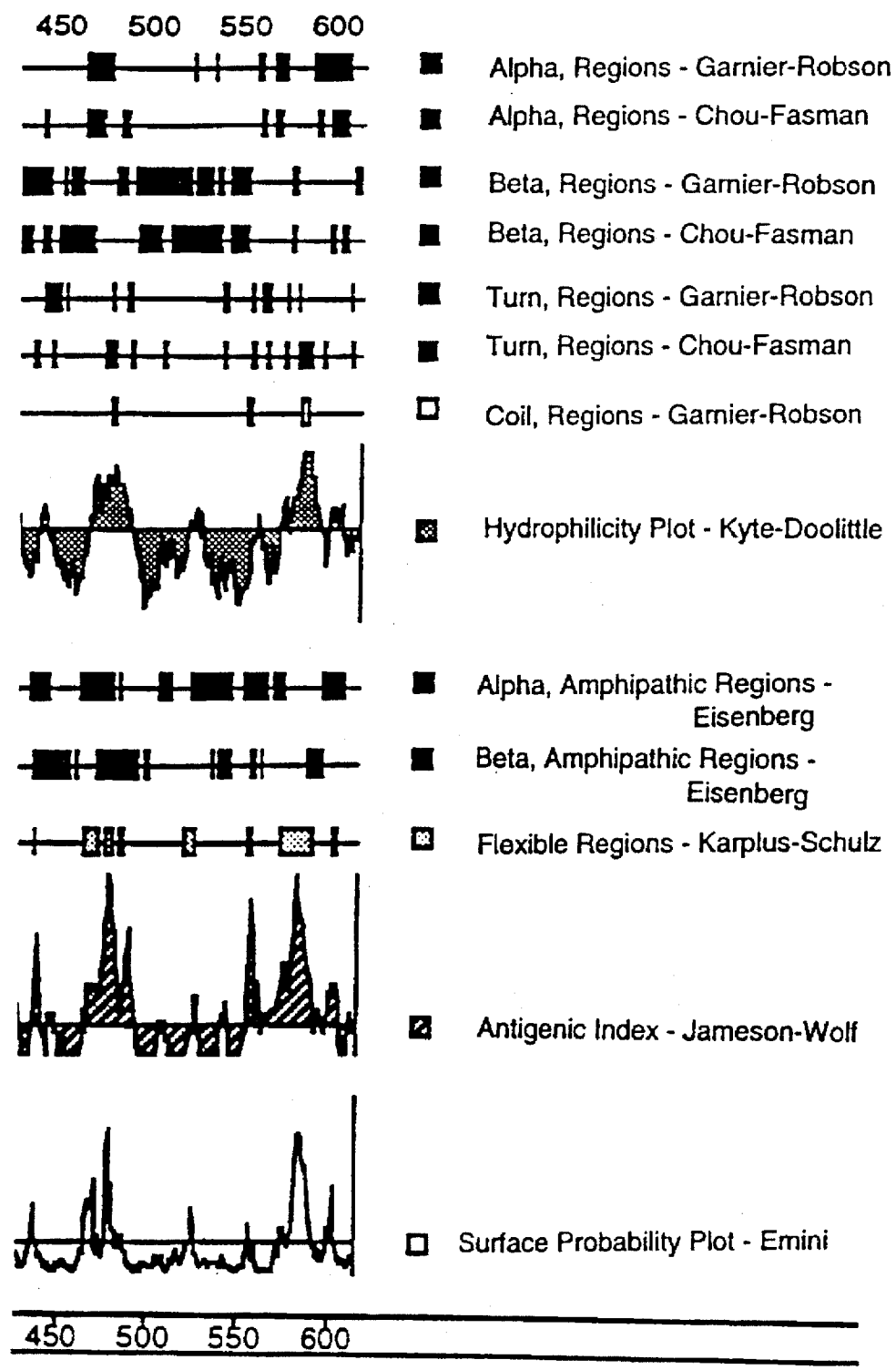

It should be pointed out that sequencing inaccuracies are a common problem which occurs in polynucleotide sequences. Accordingly, the sequence of the drawing is based on several sequencing runs and the sequencing accuracy is considered to be at least 97%.

In accordance with an aspect of the present invention, there is provided an isolated nucleic acid (polynucleotide) which encodes for the mature polypeptide having the deduced amino acid sequence of FIG. 1 (SEQ ID NO:2) or for the mature polypeptide encoded by the cDNA of the clone deposited as ATCC Deposit No. 75823 with the ATCC, 12301 Parklawn Drive, Rockville, Md. 20852 on Jun. 24, 1994. Since the strain referred to is being maintained under the terms of the Budapest Treaty, it will be made available to a patent office signatory to the Budapest Treaty.

A polynucleotide encoding a polypeptide of the present invention may be found in brain, lever and placenta. The polynucleotide of this invention was discovered in a cDNA library derived from a human brain. It is structurally related to the G protein-coupled receptor family. It contains an open reading frame encoding a protein of about 613 amino acid residues of which approximately the first 26 amino acids residues are the putative leader sequence such that the mature protein comprises 587 amino acids. The protein exhibits the highest degree of homology to a human $ET_A$ receptor with 30% identity and 55% similarity over a 420 amino acid stretch.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIG. 1 (SEQ ID NO:1) or that of the deposited clone or maybe a different coding sequence which coding sequence, as a result of the redundancy or degeneracy of the genetic code, encodes the same mature polypeptide as the DNA of FIG. 1 (SEQ ID NO:1) or the deposited cDNA.

The polynucleotide which encodes for the mature polypeptide of FIG. 1 (SEQ ID NO:2) or for the mature polypeptide encoded by the deposited cDNA may include: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIG. 1 (SEQ ID NO:2) or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIG. 1 (SEQ ID NO:2) or the same mature polypeptide encoded by the cDNA of the deposited clone as well as variants of such polynucleotides which variants encode for a fragment, derivative or analog of the polypeptide of FIG. 1 (SEQ ID NO:2) or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIG. 1 (SEQ ID NO:1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature protein, or for a protein having a prosequence or for a protein having both a prosequence and a presequence (leader sequence).

The polynucleotides of the present invention may also have the coding sequence fused in frame to a marker sequence which allows for purification of the polypeptide of the present invention. The marker sequence may be a hexahistidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37: 767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length gene of the present invention may be used as a hybridization probe for a cDNA library to isolate the full length cDNA and to isolate other cDNAs which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequence if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identify between the sequences. The polynucleotides which hybridize to the hereinabove described polynucleotides in a preferred embodiment encode polypeptides which either retain substantially the same biologically function or activity as the mature polypeptide encoded by the cDNAs of FIG. 1 (SEQ ID NO:1) or the deposited cDNA(s).

Alternatively, the polynucleotide may have at lest 20 bases, preferably 30 bases, and more preferably at least 50 bases which hybridize to a polynucleotide of the present invention and which has a identify thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

Thus, the present invention is directed to polynucleotides having at least a 70% identify, preferably at least 90% and more preferably at least a 95% identity to a polynucleotide which encodes the polypeptide of SEQ ID NO:2 as well as fragments thereof, which fragments have at least 30 bases and preferably at least 50 bases and to polypeptides encoded by such polynucleotides. The deposit(s) referred to herein will be maintained under the terms of the Budapest Treaty on the International Recognition of the Deposit of Microorganisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to a G-protein coupled receptor polypeptide which has the deduced amino acid sequence of FIG. 1 (SEQ ID NO:2) or which has the amino acid sequence encoded by the deposited cDNA, as well as fragments, analogs and derivatives of such polypeptide.

The terms "fragment," "derivative" and "analog" when referring to the polypeptide of FIG. 1 (SEQ ID NO:2) or that encoded by the deposited cDNA, means a polypeptide which either retains substantially the same biological function or activity as such polypeptide, i.e. functions as a G-protein coupled receptor, or retains the ability to bind the ligand or the receptor even though the polypeptide does not function as a G-protein coupled receptor, for example, a soluble form of the receptor. An analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIG. 1 (SEQ ID NO:2) or that encoded by the deposited cDNA may be (i) one in which one or more of the amino acid residues are substituted with a conserved or non-conversed amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide which are employed for purification of the mature polypeptide or a proprotein sequence or (v) one in which a fragment of the polypeptide is soluble, i.e. not membrane bound, yet still binds ligands to the membrane bound receptor. Such fragments, derivatives and analogs are deemed to be within the scope of those skilled in the art from the teachings, herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2 (in particular the mature polypeptide) as well as polypeptides which have at least 70% similarity (preferably at least 70% identity) to the polypeptide of SEQ ID NO:2 and more preferably at least 90% similarity (more preferably at least 90% identity) to the polypeptide of SEQ ID NO:2 and still more preferably at least 95% similarity (still more preferably at least 95% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the ETBR genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phase DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the E. coli. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as E. coli, Streptomyces, Salmonella typhimurium; fungal cells, such as yeast; insect cells such as Drosophila and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pbs, pD10, phagescript, psiX174, pbluescript SK, pbsks, pNH8A, pNH16a, pNH18A, pNH46A, (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are PKK232-8 and PCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation. (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of the replication and selectable markers permitting transfromation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals is operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis. USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, Cell, 23: 175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The G-protein coupled receptor polypeptides can be recovered and purified from recombinant cell cultures by methods including ammonium sulfate or ethanol precipitation, acid extraction, anion or cation exchange chromatography, phosphocellulose chromatography, hydrophobic interactin chromatography, affinity chromatography hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycostylated or may be non-glycosylated. Polypeptides of the invention may also include an initial methionine amino acid residue.

Bombesin, in addition to endothelin, has been found to bind to and stimulate the receptor of the present invention. Bombesin is a tetradecapeptide which has as a mammalian homolog the 27-amino acid peptide gastrin-releasing peptide (GRP). Bombesin is regarded as one of the most potent peptide to affect the central nervous system, since it has been reported as a thermoregulator in the rat (Brown, M. et al., Science, 196: 998–1000 (1977)). Also, bombesin/gastrin releasing peptide is synthesized and secreted by small cell lung cancers (Davis, T. P. et al., Peptides, 13: 401–17 (1992)).

The G-protein coupled receptor of the present invention may be employed in a process for screening for agonists and/or antagonists for the receptor.

In general, such screening procedures involve providing appropriate cells which express the receptor on the surface thereof. In particular, a polynucleotide encoding the receptor of the present invention is employed to transfect cells to thereby express the G-protein coupled receptor. Such transfection may be accomplished by procedures as hereinabove described.

One such screening procedure involves the use of a melanophore which are transfected to express the G-protein coupled receptor of the present invention. Such a screening technique is described in PCT WO 92/01810 published Feb. 6, 1992.

Thus, for example, such assay may be employed for screening for a receptor antagonist by contacting the melanophore cells which encode the G-protein coupled receptor with both the receptor ligand and a compound to be screened. Inhibition of the signal generated by the ligand indicates that a compound is a potential antagonist for the receptor, i.e., inhibits activation of the receptor.

The screen may be employed for determining an agonist by contacting such cells with compounds to be screened and determining whether such compound generates a signal, i.e., activates the receptor.

Other screening techniques include the use of cells which express the G-protein coupled receptor (for example, transfected CHO cells) in a system which measures extracellular pH changes caused by receptor activation, for example, as described in Science, volume 246, pages 181–296 (October 1989). For example, potential agonists or antagonists may be contacted with a cell which expresses the G-protein coupled receptor and a second messenger response, e.g. signal transduction or pH changes, may be measured to determine whether the potential agonist or antagonist is effective.

Another such screening technique involves introducing RNA encoding the G-protein coupled receptor into Xenopus oocytes to transiently express the receptor. The receptor oocytes may then be contacted with the receptor ligand and a compound to be screened, followed by detection of inhibition of a calcium signal.

Another screening technique involves expressing the G-protein coupled receptor in which the receptor is linked to a phospholipase C or D. As representative examples of such cells, there may be mentioned endothelial cells, smooth muscle cells, embryonic kidney cells, etc. The screening for an antagonist or agonist may be accomplished as hereinabove described by detecting activation of the receptor or inhibition of activation of the receptor from the phospholipase second signal.

Another method involves screening for antagonists by determining inhibition of binding of labeled ligand to cells which have the receptor on the surface thereof. Such a method involves transfecting a eukaryotic cell with DNA encoding the G-protein coupled receptor such that the cell expresses the receptor on its surface and contacting the cell with a potential antagonist in the presence of a labeled form of a known ligand. The ligand can be labeled, e.g., by radioactivity. The amount of labeled ligand bound to the receptors is measured, e.g., by measuring radioactivity of the receptors. If the potential antagonist binds to the receptor as determined by a reduction of labeled ligand which binds to the receptors, the binding of labeled ligand to the receptor is inhibited.

In general, antagonists for G-proteins coupled receptors which are determined by such screening procedures may be employed for a variety of therapeutic purposes. For example, such antagonists have been employed for treatment of hypertension, angina pectoris, myocardial infarction, ulcers, asthma, allergies, psychoses, depression, migraine, vomiting, and benign prostatic hypertrophy.

Agonists for G-protein coupled receptors are also useful for therapeutic purposes, such as the treatment of asthma, Parkinson's disease, acute heart failure, hypotension, urinary retention, and osteoporosis.

Examples of potential antagonists include an antibody, or in some cases an oligonucleotide, which binds to the G-protein coupled receptor but does not elicit a second messenger response such that the activity of the G-protein coupled receptor is prevented. Potential antagonists also include proteins which are closely related to the ligand of the G-protein coupled receptor, i.e. a fragment of the ligand, which have lost biological function and when binding to the G-protein coupled receptor, elicit no response.

A potential antagonist also includes an antisense construct prepared through the use of antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (tripe helix -see Lee et al., Nucl. Acids Res., 6: 3073 (1979); Cooney et al, Science, 241; 456 (1988); and Dervan et al., Science, 251: 1360 (1991)), thereby preventing transcription and the production of G-protein coupled receptor. The antisense RNA oligonucleotide hybridizes to the mRNA in vivo and blocks translation of the mRNA molecule into the G-protein coupled receptor (antisense —Okano, J. Neurochem., 56: 560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of G-protein coupled receptor.

Another potential antagonist is a small molecule which binds to the G-protein coupled receptor, making it inaccessible to ligands such that normal biological activity is prevented. Examples of small molecules include but are not limited to small peptides or peptide-like molecules.

Potential antagonists also include a soluble G-protein coupled receptor, e.g. a fragment of the receptor, which binds to the ligand and prevents the ligand from interacting with membrane bound G-protein coupled receptors.

An endothelin antagonist may be employed to offset the vasoconstrictive effects of endothelin and, therefore, may be employed to treat hypertension through vasodilation. These antagonists may also be used to treat the long-lasting vasospasms due to subarachnoid hemorrhages which cause increases in endothelin levels in cerebrospinal fluid and plasma.

Endothelin antagonists may also be employed to treat ulcerogenesis and gastric lesions. ET-1 and ET-3 induce gastric lesions and enhance alcohol-induced lesions. Accordingly, inhibiting ET-1 and ET-3 from integrating with the ETBRs can prevent these conditions.

Endothelins potently contract pulmonary smooth muscle and levels of endothelins are increased in pulmonary lavage fluid during asthmatic attacks, therefore, antagonists for diminishing or preventing binding of endothelin may be employed to treat asthma.

Endothelin levels are increased in cancer tissue and a cancer-derived cell line can be stimulated to produce endothelin. ET-1 itself stimulates growth of cancerous cells. Accordingly, endothelin antagonists may be employed to prevent the growth of cancer cells and tumors.

An increase in circulating endothelin levels is increased by ciclosporin, which may explain the toxic effects of ciclosporin. Accordingly, endothelin antagonists may be used to prevent and/or treat ciclosporin toxicity.

Endothelin antagonists may also be employed to treat septic shock which is caused by pathological levels of endothelins. Further, hypertension, congestive heart failure, coronary artery disease, atherosclerosis, restenosis, benign prostatic hypertrophy, renal failure and stroke may also be treated with the antagaonist of ETBRs.

Bombesin antagonists may be employed to treat small cell lung cancers which synthesize and secrete bombesin/gastrin releasing peptide. A bombesin antagaonist will prevent bombesin from stimulating the ETBR of the present invention.

The antagonists may be employed in a composition with a pharmaceutically acceptable carrier, e.g., as hereinafter described.

The present invention also provides a method for determining whether a ligand not known to be capable of binding to a G-protein coupled receptor can bind to such receptor which comprises contacting a mammalian cell which expresses a G-protein coupled receptor with the ligand under conditions permitting binding of ligands to the G-protein coupled receptor, detecting the presence of a ligand which binds to the receptor and thereby determining whether the ligand binds to the G-protein coupled receptor. The systems hereinabove described for determining agonists and/or antagonists may also be employed for determining ligands which bind to the receptor.

The ETBR polypeptides and antagonists or agonists may be employed in combination with a suitable pharmaceutical carrier. Such compositions comprise a therapeutically effective amount of the polypeptide, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides and agonists and antagonists may be employed in conjunction with other therapeutic compounds.

The pharmaceutical compositions may be administered in a convenient manner such as by the topical, intravenous, intraperitoneal, intramuscular, subcutaneous, intranasal or intradermal routes. The pharmaceutical compositions are administered in an amount which is effective for treating and/or prophylaxis of the specific indication. In general, the pharmaceutical compositions will be administered in an amount of at least about 10 µg/kg body weight and in most cases they will be administered in an amount not in excess of about 8 mg/Kg body weight per day. In most cases, the dosage is from about 10 µg/kg to about 1 mg/kg body weight daily, taking into account the routes of administration, symptoms, etc.

The ETBR polypeptides and antagonisms or agonists which are polypeptides, may be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproplferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and β-actin promoters). Other viral promoters which may employed include, but are not limited to, adenovirus promoters, thymidine kinase (TK) promoters, and B19 parvovirus promoters. The selection of a suitable promoter will be apparent to those skilled in the art from the teachings contained herein.

the nucleic acid sequence encoding the polypeptide of the present invention is under the control of a suitable promoter. Suitable promoters which may be employed include, but are not limited to, adenoviral promoters, such as the adenoviral major later promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the genes encoding the polypeptides.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, PG+E-86, GP+envAM12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and CaPO$_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transducer eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, kerationcytes, endothelial cells, and bronchial epithelial cells.

The present invention also provides a method for determining whether a ligand not known to be capable of binding to a G-protein coupled receptor can bind to such receptor which comprises contacting a mammalian cell which expresses a G-protein coupled receptor with the ligand under conditions permitting binding of ligands to the G-protein coupled receptor, detecting the presence of a ligand which binds to the receptor and thereby determining whether the ligand binds to the G-protein coupled receptor. The systems hereinabove described for determining agonists and/or antagonists may also be employed for determining ligands which bind to the receptor.

This invention also provides a method of detecting expression of a receptor polypeptide of the present invention on the surface of a cell by detecting the presence of mRNA coding for the receptor which comprises obtaining total mRNA from the cell and contacting the mRNA so obtained with a nucleic acid probe comprising a nucleic acid molecule of at least 10 nucleotides capable of specifically hybridizing with a sequence included within the sequence of a nucleic acid molecule encoding the receptor under hybridizing conditions, detecting the presence of mRNA hybridized to the probe, and thereby detecting the expression of the receptor by the cell.

The present invention also provides a method for identifying receptors related to the receptors polypeptides of the present invention. These related receptors may be identified by homology to a receptor polypeptide of the present invention, by low stringency cross hybridization, or by identifying receptors that interact with related natural or synthetic ligands and or elicit similar behaviors after genetic or pharmacological blockade of the receptor polypeptides of the present invention.

The present invention also contemplates the use of the genes of the present invention as a diagnostic, for example some diseases result from inherited defective genes. These genes can be detected by comparing the sequences of the defective gene with that of a normal one. Subsequently, one can verify that a "mutant" gene is associated with abnormal receptor activity. In addition, one can insert mutant receptor genes into a suitable vector for expression in a functional assay system (e.g., colorimetric assay, expression on MacConkey plates, complementation experiments, in a receptor deficient strain of HEK293 cells) as yet another means to verify or identify mutations. Once "mutant" genes have been identified, one can then screen population for carriers of the "mutant" receptor gene.

Individuals carrying mutations in the gene of the present invention may be detected at the DNA level by a variety of techniques. Nucleic acids used for diagnosis may be obtained from a patient's cells, including but not limited to such as from blood, urine, saliva, tissue biopsy and autopsy material. The genomic DNA may be used directly for detection or may be amplified enzymatically by using PCR (Saiki, et al., *Nature*, 324: 163–166 1986) prior to analysis. RNA or cDNA may also be used for the same purpose. As an example, PCR primers complimentary to the nucleic acid of the instant invention can be used to identify and analyze mutations in the gene of the present invention. For example, deletions and insertions can be detected by a change in size of the amplified product in comparison to the normal genotype. Point mutations can be identified by hybridizing amplified DNA to radio labeled RNA of the invention or alternatively, radio labeled antisense DNA sequences of the invention. Perfectly matched sequences can be distinguished from mismatched duplexes by RNase A digestion or by differences in melting temperatures. Such a diagonistic would be particularly useful for prenatal or even neonatal testing.

Sequence differences between the reference gene and "mutants" may be revealed by the direct DNA sequencing method. In addition, cloned DNA segments may be used as probes to detect specific DNA segments. The sensitivity of this method is greatly enhanced when combined with PCR. For example, a sequence primer is used with double stranded PCR product or a single stranded template molecule generated by a modified PCR. The sequence determination is performed by conventional procedures with radio labeled nucleotide or by an automatic sequencing procedure with fluorescent-tags.

Genetic testing based on DNA sequence differences may be achieved by detection of alterations in the electrophoretic mobility of DNA fragments in gels with or without denaturing agents. Sequences changes at specific locations may also be revealed by nucleus protection assays, such RNase and S1 protection or the chemical cleavage method (e.g. Cotton, et al., *PNAS, USA*, 85: 4397–4401 1985).

In addition, some diseases are a result of, or are characterized by changes in gene expression which can be detected by changes in the mRNA. Alternatively, the genes of the present invention can be used as a reference to identify individuals expressing a decrease of functions associated with receptors of this type.

The present invention also relates to a diagnostic assay for detecting altered levels of soluble forms of the receptor polypeptides of the present invention in various tissues. Assays used to detect levels of the soluble receptor polypeptides in a sample derived from a host are well known to those of skill in the art and include radioimmunoassays, competitive-binding assays, Western blot analysis and preferably as ELISA assay.

An ELISA assay initially comprises preparing an antibody specific to antigens of the receptor polypeptides, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g. a polystyrene dish, that binds the proteins in the sample. Any free proteins binding sites on the dish are then covered by incubating with a non-specific protein such as a bovine serum albumin. Next, the monoclonal antibody is incubated in the dish during which time the monoclonal antibodies attach to any receptor proteins attached to the polystyrene dish. All unbound monoclonal antibody is washed out with buffer. The reporter antibody linked to horseradish peroxidase is now placed in the dish resulting in binding of the reporter antibody to any monoclonal antibody bound to receptor proteins. Unattached reporter antibody is then washed out. Peroxidase substrates are then added to the dish and the amount of color developed in a given time period is a measurement of the amount of receptor proteins present in a given volume of patient sample when compared against a standard curve.

The sequences of the present invention are also valuable for chromosome identification. The sequence is specifically target to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the cDNA is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases. For a review of this technique, see Verma et al., Human chromosomes: a Manual of Basic Techniques, Pergamon Press, N.Y. (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coninheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256: 495–497), the trioma technique, the human B-cell hybridoma technique (Kozbor et al., 1983, Immunology Today 4: 72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 Ĭg of plasmid or DNA fragment is used with about 2 units of enzyme in about 20 Ĭl of buffer solution. For the purpose of isolating DNA fragments for plasmid construction, typically 5 to 50 Ĭg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8: 4057 (1980).

"Olginoculeotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated. "Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 µg of approximately equimolar amounts of the DNA fragments to be ligated.

Unless otherwise stated, transformation was performed as describe din the method of Graham, F. and Van der Eb, A., Virology, 52: 456–457 (1973).

EXAMPLE 1

Bacterial Expression and Purification of ETBR

The DNA sequence encoding for ETBR, ATCC #75823, is initially amplified using PCR oligonucleotide primers corresponding to the 5' and sequences of the processed ETBR protein (minus the signal peptide sequence) and the vector sequences 3' to the ETBR gene. Additional nucleotides corresponding to ETBR were added to the 5' and 3' sequences respectively. The 5' oligonucleotide primer has the sequence 5' CACTAAGCTTAATGCGAGC-CCGGGCGCG 3' (SEQ ID NO:3) contains a HindIII restriction enzyme site followed by 18 nucleotides of ETBR coding sequence starting from the presumed terminal amino acid of the processed protein codon. The 3' sequence 5' GAACTTCTAGACCGTCAGCAATGAGTACCGAC 3' (SEQ ID NO:4) contains complementary sequences to an XbaI site and is followed by 18 nucleotides of ETBR. The restriction enzyme sites correspond to the restriction enzyme sites on the bacterial expression vector pQE-9 (Qiagen, Inc. 9259 Eton Avenue, Chatsworth, Calif. 91311). pQE-9 encodes antibiotic resistance (Amp$^r$), a bacterial origin of replication (ori), an IPTG-regulatable promoter operator (P/O), a ribosome binding site (RBS), a 6-His tag and restriction enzyme sites. pQE-9 was then digested with HindIII and XbaI. The amplified sequences were ligated into pQE-9 and were inserted in frame with the sequence encoding for the histidine tag and the RBS. The ligation mixture was then used to transform E. coli HB101 by the procedure described in Sambrook, J. et al., Molecular Cloning: A laboratory Manual, Cold Spring Laboratory Press, (1989). Transformants are identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 ug/ml) and Kan (25 ug/ml) The O/N culture is used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3 to 4 hours. Cells were then harvested by centrifugation. The cell pellet was solubilized in the chaotropic agent 6 Molar Guanidine HCl. After clarification, solubilized ETBR was purified from this solution by chromatography on a Nickel-Chelate column under conditions that allow for tight binding by proteins containing the 6-His tag (Hochuli, E. et al., J. Chromatography 411: 177–184 (1984)). ETBR was eluated from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein was dialyzed to 10 mmolar sodium phosphate.

EXAMPLE 2

Expression of Recombinant ETBR in COS cells

The expression of plasmid, pETBR HA is derived from a vector pcDNAI/Amp (Invitrogen) containing: 1) SV40 origin of replication, 2) ampicillin resistance gene, 3) E. coli replication origin, 4) CMW promoter followed by a polylinker region, a SV40 intron and polyadenylation site. A DNA fragment encoding the entire ETBR protein and a HA tag fused in frame to its 3' end was cloned into the polylinker region of the vector, therefore, the recombinant protein expression is directed under the CMV promoter. The HA tag correspond to an epitope derived from the influenza hemagglutinin protein as previously described (i. Wilson, H. Niman, R. Heighten, A Cherenson, M. Connolly, and R. Lerner, 1984, Cell 37, 767). The infusion of HA tag to the target protein allows easy detection of the recombinant protein with an antibody that recognizes the HA epitope.

The plasmid construction strategy is described as follows:

The DNA sequence encoding for ETBR, ATCC #75823, was constructed by PCR on the original EST cloned using two primers: the 5' primer 5' GTCCAAGCTTGCCACCAT-GCGAGCCCCGGGCGCG 3' (SEQ ID NO:5) contains a HindIII site followed by 18 nucleotides of ETBR coding sequence starting from the initiation codon; the 3' sequence 5' CTAGCTCGAGTCAAGCGTAGTCTGG-GACGTCGTATGGGTAGCAGCAAT GAGTTCCGA-CAGA 3' (SEQ ID NO:6) contains complementary sequences to an XhoI site, translation stop condon, HA tag and the last 18 nucleotides of the ETBR coding sequence (not including the stop condon). Therefore, the PCR product contains a HindIII site, ETBR coding sequence followed by HA tag fused in frame, a translation termination stop condon next to the HA tag, and an XHoI site. The PCR amplified NA fragment and the vector, pcDNAI/Amp, were digested with HindIII and XhoI restriction enzyme and ligated. The ligation mixture was transformed into *E. coli* strain SURE (available from Stratagene Cloning Systems, 11099 North Torrey Pines Road, La Jolla, Calif. 92037) the transformed culture was plated on ampicillin media plates and resistant colonies were selected. Plasmid DNA was isolated from transformants an examined by restriction analysis for the pressure of the correct fragment. For expression of the recombinant ETBR, COS cells were transfected with the expression vector by DEAE-DEXTRAN method (J. Sambrook, E. Fritsch, T. Maniatis, Molecular Cloning: A Laboratory Manual, Cold Spring Laboratory Press, (1989)). The expression of the ETBR HA protein was detected by radiolabelling and immunoprecipitation method (E. Harlow, D. Lane, Antibodies: A Laboratory Manual, Cold Spring Harbor Laboratory Press, (1988)). Cells were labelled for 8 hours with $^{35}$S-cysteine two days post transfection. Culture media were then collected and cells were lysed with detergent (RIPA buffer (150 mM NaCl, 1% NP-40, 0.1% SDS, 1% NP-40, 0.5% DOC, 50 mM Tris, pH 7.5) (Wilson, I. et al., Id. 37: 767 (1984)). Both cell lysate and culture media were precipitated with a HA specific monoclonal antibody. Proteins precipitated were analyzed on 15% SDS-PAGE gels.

EXAMPLE 3

Cloning and expression of ETBR using the baculovirus expression system

The DNA sequence encoding the full length ETBR protein, ATCC #75823, amplified using PCR oligonucleotide primers corresponding to the 5' and 3' sequences of the gene:

The 5' primer has the sequence 5'CGGGATCCGCCAC-CATGCGAGC CCCGGGCGCG 3' (SEQ ID NO:7) and contains a BamHI restriction enzyme site (in bold) followed by 6 nucleotides resembling an efficient signal for the initiation of translation in eukaryotic cells (J. Mol. Biol. 1987, 196, 947–950, Kozak, M.) and just behind, is the first 18 nucleotides of the ETBR gene (the initiation codon for translation "ATG" is underlined).

The 3' primer has the sequence 5'CGGGATCCCGCT-CAGCAA TGAGTTCCGAC 4' (SEQ ID NO:8) and contains the cleavage site for the restriction endonuclease BamHI and 18 nucleotides complementary to the 3' non-translated sequence of the ETBR gene. The amplified sequences were isolated from a 1% agarose gel using a commercially available kit ("Geneclean," BIO 101 Inc., La Jolla, Calif.). The fragment was then digested with the endonucleases BamHI and then purified again on a 1% agarose gel. This fragment is designated F2.

The vector pRG1 (modification of pVL941 vector, discussed below) is used for the expression of the ETBR protein using the baculovirus expression system (for review see: Summers, J. D. and Smith, G. E. 1987, A manual of methods for baculovirus vectors and insect cell culture procedures, Texas Agricultural Experimental Station Bulletin No. 1555). This expression vector contains the strong polyhedrin promoter of the Autographa californica nuclear polyhedrosis virus (AcMNPV) followed by the recognition sites for the restriction endonucleases BamHI. The polyadenylation site of the simian virus (SV)40 is used for efficient polyadenylation. For an easy selection of recombinant viruses the beta-galactosidase gene from *E. coli* is inserted in the same orientation as the polyhedrin promoter followed by the polyadenylation signal of the polyhedrin gene. The polyhedrin sequences are flanked at both sides by viral sequences for the cell-mediated homologous recombination of cotransfected wild-type viral DNA. Many other baculovirus vectors could be used in place of pRG1 such as pAc373, pVL941 and pAcIM1 (Luckow, V. A. and Summers, M. D. Virology, 170: 31–39).

The plasmid was digested with the restriction enzymes BamHI and then dephosphorylated using calf intestinal phosphatase by procedures known in the art. The DNA was then isolated from a 1% agarose gel. This vector DNA is designated V2.

Fragment F2 and the dephosphorylated plasmid V2 were ligated with T4 DNA ligase. *E. coli* HB101 cells were then transformed and bacteria identified that contained the plasmid (pBacETBR) with the ETBR gene using the enzymes BamHI. The sequence of the cloned fragment was confirmed by DNA sequencing.

5 μg of the plasmid pBacETBR were cotransfected with 1.0 μg of a commercially available linearized baculovirus ("BaculoGold™ baculovirus DNA", Pharmingen, San Diego, Calif.) using the lipofectin method (Felgner et al. Proc. Natl. Acad. Sci. USA, 84: 7413–7417 (1987)).

1 μg of BaculoGold™ virus DNA and 5 μg of the plasmid pBacERBR were mixed in a sterile well of a microtiter plate containing 50 μl of serum free Grace's medium (Life Technologies Inc., Gaithersburg, Md.). Afterwards 10 μl Lipofectin plus 90 μl Grace's medium were added, mixed and incubated for 15 minutes at room temperature. Then the transfection mixture was added dropwise to the Sf9 insect cells (ATCC CRL 1711) seeded in a 35 mm tissue culture plate with 1 ml Grace' medium without serum. The plate was rocked back and forth to mix the newly added solution. The plate was then incubated for 5 hours at 27° C. After 5 hours the transfection solution was removed from the plate and 1 ml of Grace's insect medium supplemented with 10% fetal calf serum was added. The plate was put back into an incubator and cultivation continued at 27° C. for four days.

After four days the supernatant was collected and a plaque assay performed similar as described by Summers and Smith (supra). As a modification an agarose gel with "Blue Gal" (Life Technologies Inc. Gaithersburg) was used which allows an easy isolation of blue stained plaques. (A detailed description of a "plaque assay" can also be found in the user's guide for insect cell culture and baculovirology distributed by Life Technologies Inc., Gaithersburg, page 9 10).

Four days after the serial dilution, the viruses were added to the cells and blue stained plaques were picked with the tip of an Eppendorf pipette. The agar containing the recombinant viruses was then resuspended in an Eppendorf tube containing 200 μl of Grace's medium. The agar was removed by a brief centrifugation and the supernatant containing the recombinant baculoviruses was used to infect Sf9 cells seeded in 35 mm dishes. Four days later the supernatants of these culture dishes were harvested and then stored at 4° C.

Sf9 cells were grown in Grace's medium supplemented with 10% heat-inactivated FBS. The cells were infected with the recombinant baculovirus V-ETBR at a multiplicity of infection (MOI) of 2. Six hours later the medium was removed and replaced with SF900 II medium minus methionine and cysteine (Life Technologies Inc., Gaithersburg). 42 hours later 5 μCi of $^{35}$S-methionine and 5 μCi $^{35}$S cysteine (Amersham) were added. The cells were further incubated for 16 hours before they were harvested by centrifugation an the labelled proteins visualized by SDS-Page and autoradiography.

EXAMPLE 4

Xenopus Oocyte Assay to Identify Ligand

RAN was synthesized in vitro from linearized DNA, ATCC #75823, using an RNA transcription kit. This RNA was microinjected into Xenopus oocytes (10 ng of RNA/ oocytes). The oocytes were manually defolliculated prior to microinjection to remove any endogenous receptors that might be present in the follicular membranes. The injected oocytes were maintained in modified Barth's medium at 18° C. for 48 hours to allow for receptor protein expression. Electrophysiology was performed using the voltage-clamp technique. Oocytes were clamped at −60 mV and the calcium activated chloride channel activity was recorded in Barth's medium at room temperature. Data were analyzed using Axotape software.

As shown in FIG. 4, oocytes injected with the synthetic RNA complementary to DNA from ATCC #75823, illicited fairly strong Cl⁻ currents upon addition of 10 nM ET1, ET3 as well as Bombesin. Addition of ET1, ET3 and Bombesin to uninjected oocytes on the other hand did not elicit any change in membrane potential (data not shown). The ET1 and ET3 mediated response was blocked by the ET receptor peptide antagaonist BQ123. Addition of related peptide ligands like AII, Neuropeptide Y and Bradykinin did not illicit any response (FIG. 4). This indicates that the ETBR is functional and is capable of coupling to a second messenger system which leads to the mobilization of intercellular stores of calcium via production of inositol triphosphate. Since it responds to both ET and Bombesin it represents a novel endothelin-bombesin receptor.

EXAMPLE 5

Expression via Gene Therapy

Fibroblasts are obtained from a subject by skin biopsy. The resulting tissue is placed in tissue-culture medium and separated into small pieces. Small chunks of the tissue on laced on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., DNA, 7: 219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3'0 end sequences respectively. The 5' primer contains an EcorRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector has the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transducer producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

---

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 4156 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: cDNA ( x i ) SEQUENCE DESCRIPTION: SEQ ID NO:1:

| | | | | | |
|---|---|---|---|---|---|
| CCCACTATGT | TGGCCAGGAT | GGTCTTGATT | TCTTGACCTC | GTGTTCTGCC | CGCCTCTACC | 60 |
| TCCCAAAGTG | CCGGGATTAC | AGGCGTGACT | GCTGTGCCCG | GCCCCAGCAT | CACTTTTATA | 120 |
| GCTTTCTGTG | CCTCTTCCTC | TGGGCCTTGG | TGTATGAAGC | CACTTGCCTT | TCTCTGTTGG | 180 |
| GAAGCGAGCA | GAATCAGATT | GCTACTCATG | ATGCAGTCCG | GGCAGGGCAT | ACTGTCACCT | 240 |
| TTGGCTGTGG | ACACAGTTGT | CAGGATAGGG | GAGAAGCCCT | TTAGGTCCGT | CTTCTTGACA | 300 |
| CAGCCCTCCT | ACCTGGTTAC | GCTGGTGCTT | TCGCTTGGTT | TAGACAACCA | AGACACTTGA | 360 |
| GAATTATGCT | GTCCTCAGAA | TGTCTGATGA | AAAGAACAGA | TTCACTTTTT | GGACACAATG | 420 |
| CCCATTAGCC | ATCTTGGCA | GTGTTTCTGA | TCAAAGGTTC | CCCATGCCTG | CTCTAGGAAA | 480 |
| GTAAACTTTT | TTCAGAATAA | ATCCTCAAAT | GGATTACTGA | GTAGTCTTTG | CACCATTCCC | 540 |
| ATCAGCCTAA | TCAGACTGAA | TGGTCACGCT | CAGTGCAAAA | AGCTGTTTTG | CTGTTAGGAT | 600 |
| GTTTCAGTGT | TTCTTGTCTT | TCCTGGAACA | GTTCAGTTGT | TTAAATTTAG | TAATTCAATC | 660 |
| CTGACCAGTG | TAAACCCACT | TAATTATTGC | AGCCTAAAGA | ATTCAGCTAC | TTCTACTCTT | 720 |
| CATAAATGTG | CCCAAGTAAA | TATGTGTTTT | TAATATTCAA | CCCTGGAAAA | TTAGTAATTC | 780 |
| AGATGATAAA | AGCTCATGTT | TTGGTGTCTT | TGTACTCAGA | TTGTGAACAG | GCATATTTCA | 840 |
| CTGATTTAGA | CTTAGTATAC | TTGATGAGAA | TGCTCAGGTT | GAAGAGATAG | TTCTGTCAGC | 900 |
| AATCCAACAT | CTATAGCAAT | GTGGAAAAAG | TAATCAACTC | ATATTTCACG | AATTTGATGT | 960 |
| ATGTTGTGAT | TTAGAGGGCA | TGAGATAAAG | TTTATATTTG | AACTGTGTGG | GGTAGGGGA | 1020 |
| AGAAGAGGTT | GCTTAAGCAA | ATGGGGGGT | GATTGAGGAA | CAAGATGTCT | CTAAGATGAG | 1080 |
| AAGTTATTTT | CTTGCATCAT | AGAAGCACTC | TCTCCACCCG | GGAGTGATTG | TGTTAACTAT | 1140 |
| AAATCATTTA | TATCTGTACA | TTAAAGCAGA | TTCCCTCAAT | TAGGCAAATT | TGGTTAGCCA | 1200 |
| AGCCCAAGTT | ATTGTTTGTA | CTTGAAAGTA | ATAAAGCTGC | ATTTCCTTAA | AAATATATTC | 1260 |
| TGTAGTTAAG | ACTTTGTCTT | GCTTTCCGGA | ATTCCTGTTT | TTCTTTTCCT | CTAGAGACCT | 1320 |
| CGGCTTGCAA | CTGGATCAAA | CGCTGTCGAA | AGGATGTAAA | TAGGCAGAGC | AACTGTTACC | 1380 |
| AAGAAGGCCA | CCACCCCCAC | CCAAAGGCAG | TGAGGAGTGT | GGGGCTTCGT | CTGGGCTCCC | 1440 |
| CCGAGTCTCA | ACAGTAATCA | ACAGTCAGGT | GTTGATTGCA | ACTTTTCAAG | GTCAGCCACC | 1500 |
| GGGAGTAGCC | TATTCCCTCT | AGGAACCTTG | GAGGGCATAC | CTTGCTGGGA | CTCAACTTGG | 1560 |
| CTGAGAAATG | CACAAGATGC | CAAAGGAGGA | AGGATTATAG | GGGGCGTGTG | TGTGACCCCC | 1620 |
| AAGACCGATC | TTCCGCTATC | ACCCTAATCT | CCGGTTCCCC | GCTACCCGGG | CGGGGGTGAG | 1680 |
| TATGTGACAT | GTGCCTAACT | CTCAGCAGCA | ACTTCGGCAG | CAGGTGTCGA | TCCTAACTAA | 1740 |
| GCAGGAGCTG | CGGCTGCCGG | GTGTGCCCTC | ACCAAGCCAT | GCGAGCCCCG | GGCGCGCTTC | 1800 |
| TCGCCCGCAT | GTCGCGGCTA | CTGCTTCTGC | TACTGCTCAA | GGTGTCTGCC | TCTTCTGCCC | 1860 |
| TCGGGGTCGC | CCCTGCGTCC | AGAAACGAAA | CTTGTCTGGG | GGAGAGCTGT | GCACCTACAG | 1920 |
| TGATCCAGCG | CCGCGGCAGG | GACGCCTGGG | GACCGGGAAA | TTCTGCAAGA | GACGTTCTGC | 1980 |
| GAGCCCGAGC | ACCCAGGGAG | GAGCAGGGGG | CAGCGTTTCT | TGCGGGACCC | TCCTGGGACC | 2040 |
| TGCCGGCGGC | CCCGGACCGT | GACCCGGCTG | CAGGCAGAGG | GGCGGAGGCG | TCGACAGCCG | 2100 |
| GACCCCCGGG | ACCTCCAACC | AGGCCACCTG | TCCCTGGAG | GTGGAAAGGT | GCTCGGGGTC | 2160 |
| AGGAGCCTTC | TGAAACTTTG | GGGAGAGGGA | ACCCACGGC | CCTCCAGCTC | TTCCTTCAGA | 2220 |
| TCTCAGAGGA | GGAAGAGAAG | GGTCCCAGAG | GCGCTGTCAT | TTCCGGGCGT | AGCCAGGAGC | 2280 |
| AGAGTGTGAA | GACAGTCCCC | GGAGCCAGCG | ATCTTTTTTA | CTGTCCAAGG | AGAGCCGGGA | 2340 |

| | | | | | |
|---|---|---|---|---|---|
| AACTCCAGGG | TTCCCACCAC | AAGCCCCCAC | CCAAGACGGC | CAATGGACTG | GCGGGGCACG | 2400 |
| AAGGGTGGAC | AATTGCACTC | CCGGGCCGGG | CGCTGGCCCA | GAATGGATCC | TTGGGTGAAG | 2460 |
| GAATCCATGA | TCCTGGGGGT | CCCCGCCGGG | GAAACAGCAC | GAACCGGCGT | GTGAGACTGA | 2520 |
| AGAACCCCTT | CTACCCGCTG | ACCCAGGAGT | CCTATGGAGC | CTACGCGGTC | ATGTGTCTGT | 2580 |
| CCGTGGTGAT | CTTCGGGACC | GGCATCATTG | CAACCTGGC | GGTGATGTGC | ATCGTGTGCC | 2640 |
| ACAACTACTA | CATGCGGAGC | ATCTCCAACT | CCCTCTTGGC | CAACCTGGTC | TTCTGGGACT | 2700 |
| TTCTCATCAT | CTTCTTCTGC | CTTCCGCTGG | TCATCTTCCA | CGAGCTGACC | AAGAAGTGGC | 2760 |
| TGGTGGAGGA | CTTCTCCTGC | AAGATCGTGC | CCTATATAGA | GGTCGCTTCT | CTGGGAGTCA | 2820 |
| CCACTTTCAC | CTTATGTGCT | CTGTGCATAG | ACCGCTTCCG | TGCTGCCACC | AACGTACAGA | 2880 |
| TGTACTACGA | AATGATCGAA | AACTGTTCCT | CAACAACTGC | CAAACTTGCT | GTTATATGGG | 2940 |
| TGGGAGCTCT | ATTGTTAGCA | CTTCCAGAAG | TTGTTCTCCG | CCAGCTGAGC | AAGGAGGATT | 3000 |
| TGGGGTTTAG | TGGCCGAGCT | CCGGCAGAAA | GGTGCATTAT | TAAGATCTCT | CCTGATTTAC | 3060 |
| CAGACACCAT | CTATGTTCTA | GCCCTCACCT | ACGACAGTGC | GAGACTGTGG | TGGTATTTTG | 3120 |
| GCTGTTACTT | TTGTTTGCCC | ACGCTTTTCA | CCATCACCTG | CTCTCTAGTG | ACTGCGAGGA | 3180 |
| AAATCCGCAA | AGCAGAGAAA | GCCTGTACCC | GAGGGAATAA | ACGGCAGATT | CAACTAGAGA | 3240 |
| GTCAGATGAA | CTGTACAGTA | GTGGCACTGA | CCATTTATA | TGGATTGGGC | ATTATTCCTG | 3300 |
| AAAATATCTG | CAACATTGTT | ACTGCCTACA | TGGCTACAGG | GGTTTCACAG | CAGACAATGG | 3360 |
| ACCTCCTTAA | TATCATCAGC | CAGTTCCTTT | TGTTCTTTAA | GTCCTGTGTC | ACCCCAGTCC | 3420 |
| TCCTTTTCTG | TCTCTGCAAA | CCCTTCAGTC | GGGCCTTCAT | GGAGTGCTGC | TGCTGTTGCT | 3480 |
| GTGAGGAATG | CATTCAGAAG | TCTTCAACGG | TGACCAGTGA | TGACAATGAC | AACGAGTACA | 3540 |
| CCACGGAACT | CGAACTCTCG | CCTTTCAGTG | CCATACGCCG | TGAAATGTCC | ACTTTGCTT | 3600 |
| CTGTCGGAAC | TCATTGCTGA | AGGACAGTAC | TTGGTTGGGT | CAGATTTATT | TGTTTGATTT | 3660 |
| TCATATCCCG | TGAAAGTTTT | TAATTCATAT | TTTTCCTTAT | AGGGAAAAAT | GCAAAAAGA | 3720 |
| AACAATAAAG | AAAGAAATAT | TAACTACTGT | AGAACTGATT | TTACAAATTA | ATATTTGTGC | 3780 |
| TTTGAAAAAA | AGTTTCTATT | TAGTTATTTA | AGAAGAATGA | GAAGGCCAAT | AGTTTTAGAT | 3840 |
| TATTTTATCT | GGTATGGTGC | TAATATTTTA | TTTGAAAAAA | GTTACTGCAA | CTTAACTTAA | 3900 |
| AATTGCTAAC | GTTTTTTCTT | CTTTTAAAAA | TACAATTATT | GTATATTAAT | TATAGCAATG | 3960 |
| TGATTTTGTA | GGTTATTTTA | TATTTGAGTT | GTGATTGAAA | GTATGTTGTA | TATGGTATTG | 4020 |
| TGAGATGATT | TGTACTTGGA | AGCATTCACA | AAGTAGCACC | AAATAAATTA | CACTTTATTC | 4080 |
| TTTAATGTCA | TTGTCAATCT | ACTTTTAACC | AATATTCAAT | AAATCTTCTA | ATTGCCTTAA | 4140 |
| AAAAAAAAAA | AAAAAA | | | | | 4156 |

( 2 ) INFORMATION FOR SEQ ID NO:2:

( i ) SEQUENCE CHARACTERISTICS:
        ( A ) LENGTH: 613 AMINO ACIDS
        ( B ) TYPE: AMINO ACID
        ( C ) STRANDEDNESS:
        ( D ) TOPOLOGY: LINEAR ( i i ) MOLECULE TYPE: PROTEIN ( x i ) SEQUENCE DESCRIPTION: SEQ ID NO:2:

```
Met  Arg  Ala  Pro  Gly  Ala  Leu  Ala  Arg  Met  Ser  Arg  Leu  Leu
     -25            -20                      -15
Leu  Leu  Leu  Leu  Leu  Lys  Val  Ser  Ala  Ser  Ser  Ala  Leu  Gly  Val
```

```
        -10                        -5                          1
Ala  Pro  Ala  Ser  Arg  Asn  Glu  Thr  Cys  Leu  Gly  Glu  Ser  Cys  Ala
 5                       10                      15

Pro  Thr  Val  Ile  Gln  Arg  Arg  Gly  Arg  Asp  Ala  Trp  Gly  Pro  Gly
20                       25                      30

Asn  Ser  Ala  Arg  Asp  Val  Leu  Arg  Ala  Arg  Ala  Pro  Arg  Glu  Glu
35                       40                      45

Gln  Gly  Ala  Ala  Phe  Leu  Ala  Gly  Pro  Ser  Trp  Asp  Leu  Pro  Ala
50                       55                      60

Ala  Pro  Asp  Arg  Asp  Pro  Ala  Ala  Gly  Arg  Gly  Ala  Glu  Ala  Ser
65                       70                      75

Thr  Ala  Gly  Pro  Pro  Gly  Pro  Pro  Thr  Arg  Pro  Pro  Val  Pro  Trp
80                       85                      90

Arg  Trp  Lys  Gly  Ala  Arg  Gly  Gln  Glu  Pro  Ser  Glu  Thr  Leu  Gly
95                       100                     105

Arg  Gly  Asn  Pro  Thr  Ala  Leu  Gln  Leu  Phe  Leu  Gln  Ile  Ser  Glu
110                      115                     120

Glu  Glu  Glu  Lys  Gly  Pro  Arg  Gly  Ala  Val  Ile  Ser  Gly  Arg  Ser
125                      130                     135

Gln  Glu  Gln  Ser  Val  Lys  Thr  Val  Pro  Gly  Ala  Ser  Asp  Leu  Phe
140                      145                     150

Tyr  Cys  Pro  Arg  Arg  Ala  Gly  Lys  Leu  Gln  Gly  Ser  His  His  Lys
155                      160                     165

Pro  Leu  Ser  Lys  Thr  Ala  Asn  Gly  Leu  Ala  Gly  His  Glu  Gly  Trp
170                      175                     180

Thr  Ile  Ala  Leu  Pro  Gly  Arg  Ala  Leu  Ala  Gln  Asn  Gly  Ser  Leu
185                      190                     195

Gly  Glu  Gly  Ile  His  Asp  Pro  Gly  Gly  Pro  Arg  Arg  Gly  Asn  Ser
200                      205                     210

Thr  Asn  Arg  Arg  Val  Arg  Leu  Lys  Asn  Pro  Phe  Tyr  Pro  Leu  Thr
215                      220                     225

Gln  Glu  Ser  Tyr  Gly  Ala  Tyr  Ala  Val  Met  Cys  Leu  Ser  Val  Val
230                      235                     240

Ile  Phe  Gly  Thr  Gly  Ile  Ile  Gly  Asn  Leu  Ala  Val  Met  Cys  Ile
245                      250                     255

Val  Cys  His  Asn  Tyr  Tyr  Met  Arg  Ser  Ile  Ser  Asn  Ser  Leu  Leu
260                      265                     270

Ala  Asn  Leu  Val  Phe  Trp  Asn  Phe  Leu  Ile  Ile  Phe  Phe  Cys  Leu
275                      280                     285

Pro  Leu  Val  Ile  Phe  His  Gly  Leu  Thr  Lys  Lys  Trp  Leu  Val  Glu
290                      295                     300

Asp  Phe  Ser  Cys  Lys  Ile  Val  Pro  Tyr  Ile  Glu  Val  Ala  Ser  Leu
305                      310                     315

Gly  Val  Thr  Thr  Phe  Thr  Leu  Cys  Ala  Leu  Cys  Ile  Asp  Arg  Phe
320                      325                     330

Arg  Ala  Ala  Thr  Asn  Val  Gln  Met  Tyr  Tyr  Glu  Met  Ile  Glu  Asn
335                      340                     345

Cys  Ser  Ser  Thr  Thr  Ala  Lys  Leu  Ala  Val  Ile  Trp  Val  Gly  Ala
350                      355                     360

Leu  Leu  Leu  Ala  Leu  Pro  Glu  Val  Val  Leu  Arg  Gln  Leu  Ser  Lys
365                      370                     375

Glu  Asp  Leu  Gly  Phe  Ser  Gly  Arg  Ala  Pro  Ala  Glu  Arg  Cys  Ile
380                      385                     390
```

| | | | | | | | | | | | | |
|---|---|---|---|---|---|---|---|---|---|---|---|---|
| Ile 395 | Lys | Ile | Ser | Pro | Asp 400 | Leu | Pro | Asp | Thr | Ile 405 | Tyr | Val | Leu | Ala |
| Leu 410 | Thr | Tyr | Asp | Ser | Ala 415 | Arg | Lys | Trp | Trp | Tyr 420 | Phe | Gly | Cys | Tyr |
| Phe 425 | Cys | Leu | Pro | Thr | Leu 430 | Phe | Thr | Ile | Thr | Cys 435 | Ser | Leu | Val | Thr |
| Ala 440 | Arg | Lys | Ile | Arg | Lys 445 | Ala | Glu | Lys | Ala | Cys 450 | Thr | Arg | Gly | Asn |
| Lys 455 | Arg | Gln | Ile | Gln | Leu 460 | Glu | Ser | Gln | Met | Asn 465 | Cys | Thr | Val | Val |
| Ala 470 | Leu | Thr | Ile | Leu | Tyr 475 | Gly | Leu | Gly | Ile | Ile 480 | Pro | Glu | Asn | Ile |
| Cys 485 | Asn | Ile | Val | Thr | Ala 490 | Tyr | Met | Ala | Thr | Gly 495 | Val | Ser | Gln | Gln |
| Thr 500 | Met | Asp | Leu | Leu | Asn 505 | Ile | Ile | Ser | Gln | Phe 510 | Leu | Leu | Phe | Phe |
| Lys 515 | Ser | Cys | Val | Thr | Pro 520 | Val | Leu | Leu | Phe | Cys 525 | Leu | Cys | Lys | Pro |
| Phe 530 | Ser | Arg | Ala | Phe | Met 535 | Glu | Cys | Cys | Cys | Cys 540 | Cys | Cys | Glu | Glu |
| Cys 545 | Ile | Gln | Lys | Ser | Ser 550 | Thr | Val | Thr | Ser | Asp 555 | Asp | Asn | Asp | Asn |
| Glu 560 | Tyr | Thr | Thr | Glu | Leu 565 | Glu | Leu | Ser | Pro | Phe 570 | Ser | Ala | Ile | Arg |
| Arg 575 | Glu | Met | Ser | Thr | Phe 580 | Ala | Ser | Val | Gly | Thr 585 | His | Cys | | |

( 2 ) INFORMATION FOR SEQ ID NO:3:

( i ) SEQUENCE CHARACTERISTICS:
        ( A ) LENGTH: 29 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:3:

CACTAAGCTT AATGCGAGCC CCGGGCGCG 29

( 2 ) INFORMATION FOR SEQ ID NO:4:

( i ) SEQUENCE CHARACTERISTICS:
        ( A ) LENGTH: 32 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:4:

GAACTTCTAG ACCGTCAGCA ATGAGTACCG AC 32

( 2 ) INFORMATION FOR SEQ ID NO:5:

( i ) SEQUENCE CHARACTERISTICS:
        ( A ) LENGTH: 34 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:5:

GTCCAAGCTT GCCACCATGC GAGCCCGGG CGCG    34

( 2 ) INFORMATION FOR SEQ ID NO:6:

( i ) SEQUENCE CHARACTERISTICS:
        ( A ) LENGTH: 61 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:6:

CTAGCTCGAG TCAAGCGTAG TCTGGGACGT CGTATGGGTA GCAGCAATGA GTTCCGACAG    60

A    61

( 2 ) INFORMATION FOR SEQ ID NO:7:

( i ) SEQUENCE CHARACTERISTICS:
        ( A ) LENGTH: 32 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:7:

CGGGATCCGC CACCATGCGA GCCCGGGCG CG    32

( 2 ) INFORMATION FOR SEQ ID NO:8:

( i ) SEQUENCE CHARACTERISTICS:
        ( A ) LENGTH: 29 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:8:

CGGGATCCCG CTCAGCAATG AGTTCCGAC    29

---

What is claimed is:

1. An isolated polynucleotide comprising a polynucleotide sequence having at least a 95% sequence identity to a member selected from the group consisting of:
   (a) a polynucleotide encoding a polypeptide comprising amino acids 1 to 587 of SEQ ID NO:2; and
   (b) the complement of (a).

2. The isolated polynucleotide of claim 1 wherein said member is (a).

3. The isolated polynucleotide of claim 1 wherein said member is (a) and the polypeptide comprises amino acids =26 to 587 of SEQ ID NO:2.

4. The isolated polynucleotide of claim 1 comprising a polynucleotide sequence encoding a polypeptide comprising the amino acid sequence identical to amino acids 1 to 587 of SEQ ID NO:2.

5. The isolated polynucleotide of claim 1, wherein said polynucleotide is DNA.

6. The isolated polynucleotide of claim 1 comprising a polynucleotide sequence encoding a polypeptide comprising the amino acid sequence identical to amino acids –26 to 587 of SEQ ID NO:2.

7. The isolated polynucleotide of claim 1, wherein said polynucleotide is RNA.

8. A method of making a recombinant vector comprising inserting the isolated polynucleotide of claim 2 into a vector, wherein said isolated polynucleotide is DNA.

9. A recombinant vector comprising the isolated polynucleotide of claim 2, wherein said isolated polynucleotide is DNA.

10. A recombinant host cell comprising the isolated polynucleotide of claim 2, wherein said isolated polynucleotide is DNA.

11. A method for producing a polypeptide comprising expressing from the recombinant cell of claim 10 the polypeptide encoded by said polynucleotide, wherein said polypeptide produced when it has a sequence other than that of SEQ ID NO:2 will bind to a ligand which binds to a polypeptide having the sequence of SEQ ID NO:2.

12. A process for producing a polypeptide comprising:
   expressing from a recombinant cell containing the isolated polynucleotide of claim 4 the polypeptide encoded by said isolated polynucleotide.

13. A process for producing a polypeptide comprising:
   expressing from a recombinant cell containing the isolated polynucleotide of claim 6 the polypeptide encoded by said isolated polynucleotide.

14. The isolated polynucleotide of claim 1 comprising nucleotides 1794 to 3617 of SEQ ID NO:1.

15. The isolated polynucleotide of claim 1 comprising nucleotides 1779 to 3620 of SEQ ID NO:1.

16. The isolated polynucleotide of claim 1 comprising the nucleotides of the sequence of SEQ ID NO:1.

17. An isolated polynucleotide comprising a polynucleotide sequence having at least 95% sequence identity to a member selected from the group consisting of:

(a) a polynucleotide sequence encoding the same mature polypeptide encoded by the human cDNA in ATCC Deposit No. 75823; and (b) the complement of (a).

18. The isolated polynucleotide of claim 17, wherein the member is (a).

19. The isolated polynucleotide of claim 17, wherein said polynucleotide sequence comprises DNA identical to the coding portion of the human cDNA in ATCC Deposit No. 75823 which encodes a mature polypeptide.

20. A recombinant vector comprising the isolated polynucleotide of claim 17, wherein said polynucleotide is DNA.

21. A process for producing a polypeptide comprising:

expressing from a recombinant cell containing the isolated polynucleotide of claim 14 the polypeptide encoded by said isolated polynucleotide, wherein said polypeptide produced when it has a sequence other than that of SEQ ID NO:2 will bind to a ligand which binds to a polypeptide having the sequence of SEQ ID NO:2.

* * * * *

UNITED STATES PATENT AND TRADEMARK OFFICE
CERTIFICATE OF CORRECTION

PATENT NO. : 5,750,370
DATED : May 12, 1998
INVENTOR(S) : Yi Li, et al

It is certified that error appears in the above-identified patent and that said Letters Patent is hereby corrected as shown below:

Title page, item [54] and column 1, lines 1-3, should read as follows:
NUCLEIC ACID ENCODING HUMAN ENDOTHELIN-BOMBESIN RECEPTOR AND METHOD OF PRODUCING THE RECEPTOR Signed and Sealed this Third Day of November, 1998

*Attest:*

BRUCE LEHMAN

*Attesting Officer*  *Commissioner of Patents and Trademarks*